(12) United States Patent
Skalla et al.

(10) Patent No.: US 8,470,355 B2
(45) Date of Patent: Jun. 25, 2013

(54) MESH IMPLANT

(75) Inventors: Walter Skalla, Old Lyme, CT (US);
Nathaniel Mast, Hamden, CT (US)

(73) Assignee: Covidien LP, Mansfield, MA (US)

( * ) Notice: Subject to any disclaimer, the term of this patent is extended or adjusted under 35 U.S.C. 154(b) by 87 days.

(21) Appl. No.: 12/888,084

(22) Filed: Sep. 22, 2010

(65) Prior Publication Data

US 2011/0081397 A1 Apr. 7, 2011

Related U.S. Application Data

(60) Provisional application No. 61/247,711, filed on Oct. 1, 2009.

(51) Int. Cl.
*A61M 31/00* (2006.01)
*A61B 17/00* (2006.01)

(52) U.S. Cl.
USPC .............................. 424/423; 424/22; 606/151

(58) Field of Classification Search
USPC .............................................. 604/515; 623/1
See application file for complete search history.

(56) References Cited

U.S. PATENT DOCUMENTS

| | | | |
|---|---|---|---|
| 3,364,200 A | 1/1968 | Ashton et al. | |
| 3,666,750 A | 5/1972 | Briskin et al. | |
| 3,937,223 A | 2/1976 | Roth | |
| 4,511,478 A | 4/1985 | Nowinski et al. | |
| 4,626,253 A | 12/1986 | Broadnax, Jr. | |
| 4,663,163 A | 5/1987 | Hou et al. | |
| 4,826,945 A | 5/1989 | Cohn et al. | |
| 4,938,763 A | 7/1990 | Dunn et al. | |
| 5,100,992 A | 3/1992 | Cohn et al. | |
| 5,160,745 A | 11/1992 | DeLuca et al. | |
| 5,410,016 A | 4/1995 | Hubbell et al. | |
| 5,484,913 A | 1/1996 | Stilwell et al. | |
| 5,505,952 A | 4/1996 | Jiang et al. | |
| 5,514,379 A | 5/1996 | Weissleder et al. | |
| 5,527,864 A | 6/1996 | Suggs et al. | |
| 5,580,923 A | 12/1996 | Yeung et al. | |
| 5,626,863 A | 5/1997 | Hubbell et al. | |
| 5,643,596 A | 7/1997 | Pruss et al. | |
| 5,645,849 A | 7/1997 | Pruss et al. | |
| 5,752,974 A | 5/1998 | Rhee et al. | |
| 5,851,229 A * | 12/1998 | Lentz et al. ................ | 623/23.72 |
| 6,152,943 A | 11/2000 | Sawhney | |
| 6,162,241 A | 12/2000 | Coury et al. | |
| 6,165,201 A | 12/2000 | Sawhney et al. | |
| 6,179,862 B1 | 1/2001 | Sawhney | |
| 6,500,777 B1 | 12/2002 | Wiseman et al. | |
| 6,514,534 B1 | 2/2003 | Sawhney | |
| 6,566,406 B1 | 5/2003 | Pathak et al. | |
| 6,605,294 B2 | 8/2003 | Sawhney | |
| 6,673,093 B1 | 1/2004 | Sawhney | |
| 6,703,047 B2 | 3/2004 | Sawhney et al. | |
| 6,800,753 B2 | 10/2004 | Kumar | |
| 6,818,018 B1 | 11/2004 | Sawhney | |
| 6,833,408 B2 | 12/2004 | Sehl et al. | |
| 6,936,005 B2 | 8/2005 | Poff et al. | |
| 6,969,400 B2 | 11/2005 | Rhee et al. | |
| 7,009,034 B2 | 3/2006 | Pathak et al. | |
| 7,052,713 B2 | 5/2006 | Stimmeder | |
| 7,176,256 B2 | 2/2007 | Rhee et al. | |
| 7,347,850 B2 | 3/2008 | Sawhney | |
| 2002/0010457 A1 * | 1/2002 | Duchon et al. ................ | 604/515 |
| 2002/0106409 A1 | 8/2002 | Sawhney et al. | |
| 2003/0035786 A1 | 2/2003 | Hendriks et al. | |
| 2003/0073663 A1 | 4/2003 | Wiseman et al. | |
| 2004/0001879 A1 | 1/2004 | Guo et al. | |
| 2004/0023842 A1 | 2/2004 | Pathak et al. | |
| 2004/0101546 A1 | 5/2004 | Gorman et al. | |
| 2004/0191277 A1 | 9/2004 | Sawhney et al. | |
| 2004/0265371 A1 | 12/2004 | Looney et al. | |
| 2005/0249772 A1 * | 11/2005 | Malaviya et al. ............. | 424/423 |
| 2006/0034930 A1 | 2/2006 | Khosravi et al. | |
| 2006/0159733 A1 | 7/2006 | Pendharkar et al. | |
| 2006/0233869 A1 | 10/2006 | Looney et al. | |
| 2007/0014862 A1 | 1/2007 | Pameijer et al. | |
| 2007/0123817 A1 | 5/2007 | Khosravi et al. | |
| 2007/0190110 A1 | 8/2007 | Pameijer et al. | |
| 2007/0275073 A1 | 11/2007 | Huey et al. | |
| 2008/0027365 A1 | 1/2008 | Huey et al. | |
| 2008/0114092 A1 | 5/2008 | Sawhney | |
| 2008/0160051 A1 | 7/2008 | Sirota | |
| 2008/0194805 A1 | 8/2008 | Vignon et al. | |
| 2009/0215923 A1 * | 8/2009 | Carnahan et al. ............. | 523/118 |

FOREIGN PATENT DOCUMENTS

| | | |
|---|---|---|
| EP | 0627911 | 10/2000 |
| EP | 2 143 737 A1 | 1/2010 |
| EP | 2 196 193 A1 | 6/2010 |
| EP | 2 233 160 A2 | 9/2010 |
| EP | 2 233 161 A2 | 9/2010 |
| WO | WO 94/03155 | 2/1994 |

OTHER PUBLICATIONS

International Search Report issued in Application EP 11250562.3 mailed Dec. 8, 2011.
International Search Report issued in Application EP 11250564.9 mailed Dec. 8, 2011.
International Search Report issued in Application EP 11250563.1 mailed Dec. 27, 2011.
International Search Report issued in Application EP 11250566.4 mailed Dec. 22, 2011.
International Search Report issued in Application EP 11250565.6 mailed Dec. 23, 2011.

* cited by examiner

*Primary Examiner* — Walter Webb

(57) ABSTRACT

The present disclosure relates to implants including a porous substrate, a first hydrogel precursor, a second hydrogel precursor and a mesh. The first and second hydrogel precursors are applied to the porous substrate. The mesh has a first portion in contact with the porous substrate and a second portion exposed for tissue contact.

23 Claims, 7 Drawing Sheets

MESH IMPLANT

CROSS-REFERENCE TO RELATED APPLICATION

The present application claims the benefit of and priority to U.S. Provisional Application Ser. No. 61/247,711, filed on Oct. 1, 2009, the entire disclosure of which is incorporated herein by reference.

BACKGROUND

1. Technical Field

The present disclosure relates to implants which include a mesh and a porous substrate having a first hydrogel precursor and a second hydrogel precursor applied thereto.

2. Background of Related Art

A hernia is a protrusion of a tissue, structure, or part of an organ through injured muscle tissue or an injured membrane by which the tissue, structure, or organ is normally contained. Some examples of hernias include: abdominal hernias, diaphragmatic hernias and hiatal hernias (for example, paraesophageal hernia of the stomach), pelvic hernias, for example, obturator hernia, anal hernias, hernias of the nucleus pulposus of the intervertebral discs, intracranial hernias, and Spigelian hernias.

Hernias may be surgically repaired, and are principally repaired by pushing back, or "reducing", the herniated tissue, and then reinforcing the defect in injured muscle tissue (an operation called herniorrhaphy). Modern muscle reinforcement techniques involve placement of an implant, such as a surgical mesh, near the injured tissue or defect to support the defect. The implant is either placed over the defect (anterior repair) or more often under the defect (posterior repair).

A variety of different fixation devices are used to anchor the implant into the tissue. For example, a needled suture may be passed through or around the tissue near the defect to hold the implant in a position which spans the injured tissue. In other examples, staples, tacks, clips and pins are also known to be passed through or around the tissue near the defect to anchor the implant in a position which spans the injured tissue. Although such methods have been proven effective in anchoring the implant into the tissue, penetration of the tissue by such devices may inflict addition trauma to the defect or the tissue near the defect and requires additional time for healing of the tissue.

Therefore it would be desirable to provide an implant which does not require the additional use of a fixation device, but rather is self-positioning. The combination of a mesh with a porous substrate which includes adhesive materials activated by the presence of aqueous physiological fluids ensures the in situ adherence of the device at the site of implantation thereby anchoring the implant without inflicting additional trauma to the injured tissue.

SUMMARY

The present implants include a porous substrate, a first hydrogel precursor, a second hydrogel precursor, and a mesh. The first and second hydrogel precursors are applied to the porous substrate. The mesh has a first portion in contact with the porous substrate and a second portion exposed for tissue contact. In some embodiments, at least one of the first or second hydrogel precursors may be applied to the porous substrate as a film. In some embodiments, the first hydrogel precursor may be spatially separated from the second hydrogel precursor to prevent the first and second hydrogel precursors from reacting with each other until the implant is placed at the site of implantation and exposed to the physiological fluids of a patient. Exposure of the implant to physiological fluids may cause the first hydrogel precursor to migrate through the porous substrate to react with the second hydrogel precursor. In certain embodiments, the present implants display not only adhesive properties but further display hemostatic properties.

Methods for supporting tissue are also described. In accordance with the present methods, an implant having a porous substrate, a first hydrogel precursor, a second hydrogel precursor, and a mesh, may be positioned in contact with a physiological fluid of a patient. The implant may be positioned over the injured tissue and then contacted with the patient's tissue so that physiological fluids are wicked through the porous substrate sequentially dissolving the first hydrogel precursor and then the second hydrogel precursor coating. Once dissolved, the first and second hydrogel precursors react to form a biocompatible crosslinked adhesive material. The adhesive material anchors the porous substrate to the tissue with the mesh spanning across the injured tissue and supporting the injured tissue. In some embodiments, the first hydrogel precursor may be applied as a film to a first portion of the substrate. Upon contact with physiological fluids, the film dissolves and the first precursor is wicked into the porous substrate into contact with the second hydrogel precursor to form a biocompatible crosslinked material.

BRIEF DESCRIPTION OF THE DRAWINGS

Various embodiments of the present disclosure will be discussed in more detail below in conjunction with selected embodiments and the appended drawings wherein.

DETAILED DESCRIPTION

Figure 1A:
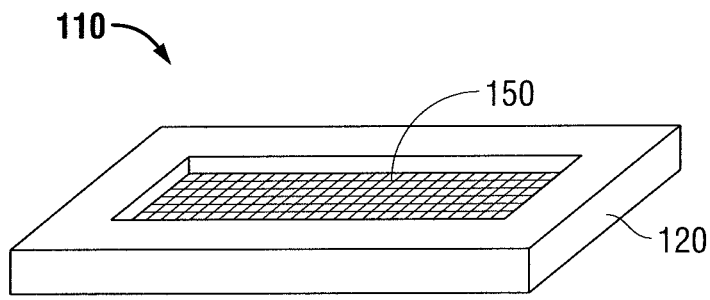
FIG. 1A shows a perspective view of one embodiment of a mesh implant according to the present disclosure.

Implants in accordance with the present disclosure include a porous substrate, a first hydrogel precursor, a second hydrogel precursor, and a mesh. The first and second hydrogel precursors may be applied to the porous substrate. The mesh has a first portion in contact with the porous substrate and a second portion exposed for tissue contact. During use, the first and second hydrogel precursors react upon exposure to physiological fluids to provide hemostasis and anchor the implant in the injured tissue to allow the mesh to support injured tissue. In some embodiments, the first and second hydrogel precursors may be distinguishable from one another by the addition of contrast dyes, surface texturing, coloring or other visual cues. In some embodiments, the first and second hydrogel precursors may be positioned on different portions of the porous substrate. Upon contact with tissue, such as, for example, injured tissue, the implant may soak up physiological fluid and the first hydrogel precursor may be dissolved by the fluid. As the fluid wicks into and migrates across the porous implant, it will carry the dissolved first hydrogel precursor along through the implant. Eventually, the fluid will migrate through the implant sufficiently to reach the second portion to which the second hydrogel precursor may be applied, thereby dissolving the second hydrogel precursor. The first and second hydrogel precursors may then react to form a biocompatible cross-linked material, thereby anchoring the implant in the tissue and also assisting with hemostasis.

The porous substrate of the implant has openings or pores over at least a portion of a surface thereof. The pores may be formed in the substrate either before or after implantation. As described in more detail below, suitable materials for forming the porous substrate include, but are not limited to fibrous structures (e.g., knitted structures, woven structures, non-woven structures, etc.) and/or foams (e.g., open or closed cell foams). In some embodiments, the pores may be in sufficient number and size so as to interconnect across the entire thickness of the porous substrate. Woven fabrics, knitted fabrics and open cell foams are illustrative examples of structures in which the pores can be in sufficient number and size so as to interconnect across the entire thickness of the porous substrate. In other embodiments, the pores do not interconnect across the entire thickness of the porous substrate. Closed cell foams or fused non-woven materials are illustrative examples of structures in which the pores may not interconnect across the entire thickness of the porous substrate. The pores of the foam porous substrate may span across the entire thickness of porous substrate. In yet other embodiments, the pores may not extend across the entire thickness of the porous substrate, but rather may be present at a portion of the thickness thereof. In embodiments, the openings or pores may be located on a portion of the surface of the porous substrate, with other portions of the porous substrate having a non-porous texture. In other embodiments, the pores may be formed after implantation in situ. The in situ pore formation may be performed using any suitable method. Some non-limiting examples include the use of contact lithography, lyophilization, living radical photopolymer (LRPP) systems and salt leaching. Those skilled in the art reading the present disclosure will envision other methods for making pore distribution patterns and configurations for the porous substrate.

Where the porous substrate is fibrous, the fibers may be filaments or threads suitable for knitting or weaving or may be staple fibers, such as those frequently used for preparing non-woven materials. The fibers may be made from any biocompatible material. Thus, the fibers may be formed from a natural material or a synthetic material. The material from which the fibers are formed may be bioabsorbable or non-bioabsorbable. It should of course be understood that any combination of natural, synthetic, bioabsorbable and non-bioabsorbable materials may be used to form the fibers. Some non-limiting examples of materials from which the fibers may be made include, but are not limited to poly(lactic acid), poly(glycolic acid), poly(lactide, poly(glycolide). Poly(trimethylene carbonate), poly(dioxanone), poly(hydroxybutyrate), poly(phosphazine), polyesters, polyethylene terephthalate, ultra-high molecular weight polyethylene, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly (amino acids), copoly(ether-esters), polyalkylene oxalates, poly(saccharides), polyamides, poly(iminocarbonates), polyalkylene oxalates, polyoxaesters, polyorthoesters, polyphosphazenes, biopolymers, polymer drugs and copolymers, block copolymers, homopolymers, blends and combinations thereof.

Where the porous substrate is fibrous, the porous substrate may be formed using any method suitable to forming fibrous structures, including but not limited to knitting, weaving, non-woven techniques, wet-spinning, electro-spinning, extrusion, co-extrusion, and the like. Suitable techniques for making fibrous structures are within the purview of those skilled in the art.

In some embodiments, the porous substrate may be made from fibers of oxidized cellulose. Such materials are known and include oxidized cellulose hemostat materials commercially available under the trade name SURGICEL®. Methods for preparing oxidized cellulose hemostat materials are known to those skilled in the art and are disclosed, for example in U.S. Pat. Nos. 3,364,200; 4,626,253; 5,484,913; and 6,500,777, the disclosures of which are incorporated herein by this reference in their entirety.

Where the porous substrate is a foam, the porous substrate may be formed using any method suitable to forming a foam or sponge including, but not limited to the lyophilization or freeze-drying of a composition. The foam may be cross-linked or non-cross-linked, and may include covalent or ionic bonds. Suitable techniques for making foams are within the purview of those skilled in the art.

The porous substrate may be at least 0.1 cm thick, in embodiments from about 0.2 to about 1.5 cm thick. The size of the pores in the porous substrate may be from about 2 μm to about 300 μm, in embodiments from about 50 μm to about 150 μm. It is envisioned that the pores of the substrate may be arranged in any manner in the substrate. For example, the pores may be configured in a random or uniform manner. In some embodiments, the pores may be formed with the use of copper alginate to create a honey-comb shaped porous substrate. In still other embodiments, the pores may be configured to create a gradient in the porous substrate. The gradient may further enhance the porous substrates ability to absorb the physiologic fluid and direct the migration of the physiological fluid carrying the first hydrogel precursor towards the second hydrogel precursor.

In embodiments, the implant may be made from non-denatured collagen or collagen which has at least partially lost its helical structure through heating or any other method, consisting mainly of non-hydrolyzed α chains, of molecular weight close to 100 kDa. The term "non-denatured collagen"

means collagen which has not lost its helical structure. The collagen used for the implant of present implant may be native collagen or atelocollagen, notably as obtained through pepsin digestion and/or after moderate heating as defined previously. The collagen may have been previously chemically modified by oxidation, methylation, ethylation, succinylation or any other known process. The collagen may also be cross-linked with any suitable crosslinker, such as genipin, isocyanates, and aldehydes. The origin and type of collagen may be as indicated for the non-implant described above.

In embodiments, the implant may be obtained by freeze-drying an aqueous acid solution of collagen at a concentration of 2 to 50 g/l and an initial temperature of 4 to 25° C. The concentration of collagen in the solution may be from about 1 g/l to about 30 g/l, in embodiments about 10 g/l. This solution is advantageously neutralized to a pH of around 6 to 8.

The implant may also be obtained by freeze-drying a fluid foam prepared from a solution of collagen or heated collagen, emulsified in the presence of a volume of air in variable respective quantities (volume of air:water varying from about 1 to about 10).

The porous substrate has a first hydrogel precursor applied thereto and a second hydrogel precursor applied thereto. The terms "first hydrogel precursor" and "second hydrogel precursor" each means a polymer, functional polymer, macromolecule, small molecule, or crosslinker that can take part in a reaction to form a network of crosslinked molecules, e.g., a hydrogel.

In embodiments, at least one of the first or second hydrogel precursors may be a small molecule of about 1000 Da or less, and is referred to as a "crosslinker". The crosslinker may have a solubility of at least 1 g/100 mL in an aqueous solution. A crosslinked molecule may be crosslinked via an ionic or covalent bond, a physical force, or other attraction.

In embodiments, at least one of the first or second hydrogel precursors may be a macromolecule, and is referred to as a "functional polymer". The macromolecule, when reacted in combination with a crosslinker, may be at least five to fifty times greater in molecular weight than the small molecule crosslinker and can be less than about 60,000 Da. In some embodiments, a macromolecule that is seven to thirty times greater in molecular weight than the crosslinker may be used and, in some embodiments a macromolecule that is about ten to twenty times difference in weight may be used. Further, a macromolecular molecular weight of 5,000 Da to 50,000 Da may be useful. The term polymer, as used herein, means a molecule formed of at least three repeating groups.

Each of the first and second hydrogel precursors is multi-functional, meaning that it comprises two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form crosslinked polymeric products. Such reactions are referred to as "crosslinking reactions".

In certain embodiments, each of the first and second hydrogel precursors includes only one category of functional groups, either only nucleophilic groups or only electrophilic functional groups, so long as both nucleophilic and electrophilic precursors are used in the crosslinking reaction. Thus, for example, if the first hydrogel precursor has nucleophilic functional groups such as amines, the second hydrogel precursor may have electrophilic functional groups such as N-hydroxysuccinimides. On the other hand, if first hydrogel precursor has electrophilic functional groups such as sulfosuccinimides, then the second hydrogel precursor may have nucleophilic functional groups such as amines or thiols. Thus, functional polymers such as proteins, poly(allyl amine), styrene sulfonic acid, or amine-terminated di- or multifunctional poly(ethylene glycol) ("PEG") can be used.

The first and second hydrogel precursors may have biologically inert and water soluble cores. When the core is a polymeric region that is water soluble, polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly(saccharides), such as dextran, chitosan, alginates, carboxymethylcellulose, oxidized cellulose, hydroxyethylcellulose, hydroxymethylcellulose, hyaluronic acid, and proteins such as albumin, collagen, casein, and gelatin. The polyethers and more particularly poly(oxyalkylenes) or poly(ethylene glycol) or polyethylene glycol are especially useful. When the core is small molecular in nature, any of a variety of hydrophilic functionalities can be used to make the first and second hydrogel precursors water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

If it is desired that the biocompatible crosslinked polymer resulting from the reaction of the first and second hydrogel precursors be biodegradable or absorbable, one or more of the first and second hydrogel precursors may have biodegradable linkages present between the functional groups. The biodegradable linkage optionally also may serve as the water soluble core of one or more of the precursors. In the alternative, or in addition, the functional groups of the first and second hydrogel precursors may be chosen such that the product of the reaction between them results in a biodegradable linkage. For each approach, biodegradable linkages may be chosen such that the resulting biodegradable biocompatible crosslinked polymer will degrade, dissolve or be absorbed in a desired period of time. In embodiments, biodegradable linkages may be selected that degrade under physiological conditions into non-toxic products.

The biodegradable linkage may be chelates or chemically or enzymatically hydrolyzable or absorbable. Illustrative chemically hydrolyzable biodegradable linkages include polymers, copolymers and oligomers of glycolide, dl-lactide, 1-lactide, caprolactone, dioxanone, and tritnethylene carbonate. Illustrative enzymatically hydrolyzable biodegradable linkages include peptidic linkages cleavable by metalloproteinases and collagenases. Additional illustrative biodegradable linkages include polymers and copolymers of poly(hydroxy acid)s, poly(orthocarbonate)s, poly(anhydride)s, poly(lactone)s, poly(amino acid)s, poly(carbonate)s, poly(saccharide)s, poly(phosphonate)s, and combinations thereof.

In embodiments, the biodegradable linkage may contain ester linkages. Some non-limiting examples include esters of succinic acid, glutaric acid, propionic acid, adipic acid, or amino acids, as well as carboxymethyl esters.

In embodiments, a multifunctional nucleophilic polymer such as trilysine may be used as a first hydrogel precursor and a multifunctional electrophilic polymer such as a multi-aim PEG functionalized with multiple NHS groups may be used as a second hydrogel precursor. The multi-arm PEG functionalized with multiple NHS groups can for example have four, six or eight and have a molecular weight of from about 5,000 Da to about 25,000 Da. Many other examples of suitable first and second precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire content of each of which is incorporated herein by reference.

The first hydrogel precursor may be applied to a first portion of the porous substrate and a second hydrogel precursor applied to a second portion of the porous substrate. For example, the precursors may be applied in a dry form, such as particulate matter or in a solid or semi-solid state such as a film, or foam. In embodiments, at least one of the first or second hydrogel precursors may be applied to the porous substrate as a film. In embodiments, the first portion of the substrate having the first hydrogel precursor applied thereto may be spatially separated from the second portion of the porous substrate having the second hydrogel precursor applied thereto. Having the first and second hydrogel precursors spatially separated from each other prevents them from reacting with each other until the implant is placed at the site of implantation and exposed to the physiological fluids of a patient.

In embodiments, the first hydrogel precursor may be applied to the porous substrate using any suitable method known to those skilled in the art. For example, the first hydrogel precursor may be incorporated into the porous substrate prior to forming the porous substrate. In another non-limiting example, the first hydrogel precursor may be positioned in the pores of the porous substrate or onto a surface of the porous substrate following formation of the substrate. In additional embodiments, the porous substrate may be calendered prior to application of the first hydrogel precursor thereby allowing the first precursor to penetrate into openings on the substrate which were created by the calendaring process. In still other embodiments, the first hydrogel precursor may be applied to the porous substrate in solution followed by evaporation or lyophilization of the solvent.

The second hydrogel precursor likewise may be applied to the porous substrate using any suitable method known to those skilled in the art. In some embodiments, it is envisioned that a coating may be applied to the substrate in any concentration, dimension and configuration capable of forming an implant. In embodiments, the second hydrogel precursor coating may penetrate the pores of the porous substrate. The coating may form a non-porous layer or a porous layer.

In some embodiments, the first hydrogel precursor may be applied to the porous substrate in a solution. In some embodiments, the second hydrogel precursor may be applied to the porous substrate in a solution. The first and second hydrogel precursors may be solubilized in any suitable solvent. Some examples of suitable solvents include, but are not limited to, water, saline, N-methyl-2-pyrrolidone, 2-pyrrolidone, $C_2$ to $C_6$ alkanols, propylene glycol, acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsufoxide, oleic acid, propylene carbonate, aromatic amides such as N,N-diethyl-m-toluamide, 1-dodecylazacycloheptan-2-one, and the like. The solvent may be removed from the porous substrate, leaving the first and/or second hydrogel precursor positioned in the porous substrate in a particle or dehydrated form. The solvent may be removed using any method suitable for drying or driving off the solvent.

In addition to the porous substrate, the implants described herein include a mesh useful for supporting injured tissue and tissue ingrowth. The mesh, like the porous substrate, may be made from fibrous materials, the fibers may be filaments or threads suitable for knitting or weaving or may be staple fibers, such as those frequently used for preparing non-woven materials. The fibers may be made from any biocompatible material. The fibers may be formed from a natural material or a synthetic material. The material from which the fibers are formed may be bioabsorbable or non-bioabsorbable. It should of course be understood that any combination of natural, synthetic, bioabsorbable and non-bioabsorbable materials may be used to form the fibers. Some non-limiting examples of materials from which the fibers may be made include, but are not limited to poly(lactic acid), poly(glycolic acid), poly(lactide, poly(glycolide). Poly(trimethylene carbonate), poly(dioxanone), poly(hydroxybutyrate), poly (phosphazine), polyesters, polyethylene terephthalate, ultra-high molecular weight polyethylene, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, poly(saccharides), polyamides, poly(iminocarbonates), polyalkylene oxalates, polyoxaesters, polyorthoesters, polyphosphazenes, biopolymers, polymer drugs and copolymers, block copolymers, homopolymers, blends and combinations thereof.

The mesh may be formed using any method suitable to forming fibrous structures, including but not limited to knitting, weaving, non-woven techniques, and the like. Suitable techniques for making the mesh are within the purview of those skilled in the art. In embodiments, the mesh has a three dimensional structure, such as the knitted textiles described in U.S. Pat. Nos. 7,021,086 and 6,443,964 the disclosures of which are incorporated herein by this reference in their entirety.

In addition to providing tissue support and hemostasis, the implants may further be used for delivery of a bioactive agent. Thus, in some embodiments, at least one bioactive agent may be combined with any part of the implant including the porous substrate, the first hydrogel precursor, the second hydrogel precursor, the mesh and/or may be separately applied to the implant. The agents may be freely admixed with the precursors or may be tethered to the precursors through any variety of chemical bonds. In these embodiments, the present implant may also serve as a vehicle for delivery of the bioactive agent.

The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present implant in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implant and the surrounding tissues opposite the target tissue. In addition, anti-adhesive agents may be used to prevent adhesions from forming between the implant and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent in the implants described herein include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the implants of the present disclosure.

Other bioactive agents which may be included as a bioactive agent in any portion of the implants in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in the implants described herein include viruses and cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons $\beta$-IFN, ($\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

Figure 1B:
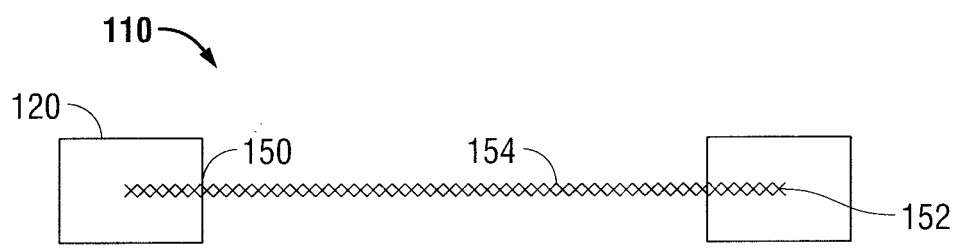
FIG. 1B shows a cross-sectional view of the implant of FIG. 1A as described in at least one of the embodiments in the present disclosure.

Turning now to FIGS. 1A and 1B, implant 110 is shown which includes porous substrate 120 and mesh 150. Porous substrate 120 includes a first hydrogel precursor and second hydrogel precursor and is positioned around the perimeter of mesh 150. Mesh 150 includes first portion 152 which is embedded in porous substrate 120 and a second portion 154 which is free of substrate 120 and able to interact with the surrounding tissue when implanted. During use, the first and second hydrogel precursors interact upon implantation to form a material useful for anchoring the porous substrate to tissue. The material may also provide hemostasis to the site of implantation.

Figure 2A:
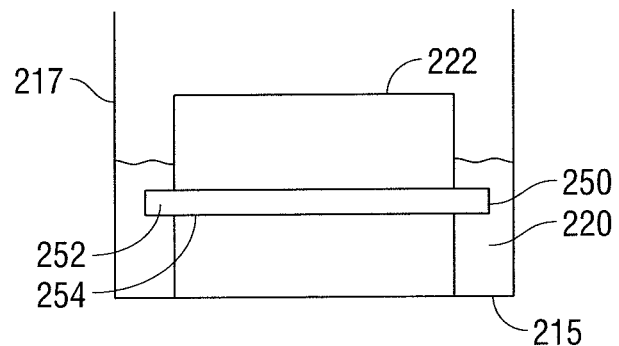
FIGS. 2A and 2B schematically show incorporation of a mesh into a porous substrate as described in at least one of the embodiments in the present disclosure.
Figure 2B:
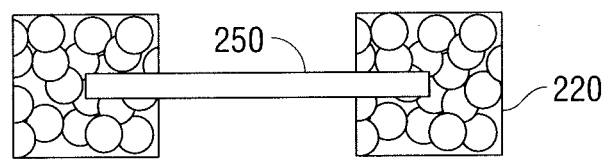
Figure 2C:
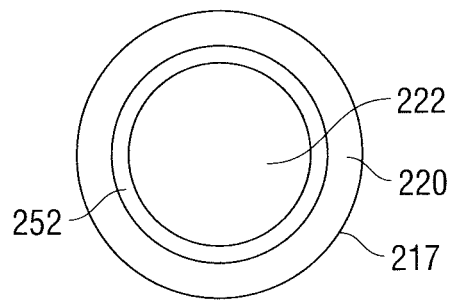
FIG. 2C is a top view of the implant of FIG. 2A as described in at least one of the embodiments in the present disclosure.

FIGS. 2A-2C show a sequence wherein mesh 250 is incorporated into porous substrate 220 via lyophilization. In FIGS. 2A and 2C, mesh 250 is positioned in mold 222 located in container 215. Mesh 250 may be larger than mold 222, so a first portion 252 of mesh 250 extends past the perimeter of mold 222. Mold 222 also stores second portion 254 of mesh 250 and prevents second portion 254 of mesh 250 from interacting with porous substrate 220. Porous substrate 220, in liquid form, is positioned between mold 222 and outer wall 217 of container 215 to a depth greater than mesh 250 and lyophilized to form a porous foam with a portion of a mesh incorporated therein (see FIG. 2B). The size, shape and dimension of container 215, outer wall 217, and mold 222 may vary thereby creating a porous substrate of any shape suitable for implantation.

In embodiments, the first hydrogel precursor and second hydrogel precursor may be combined with the liquid material used to form the porous substrate prior to lyophilization. In embodiments, the first and second hydrogel precursors may be added to porous substrate following the formation of the porous substrate or the incorporation of the mesh.

Figure 3A:
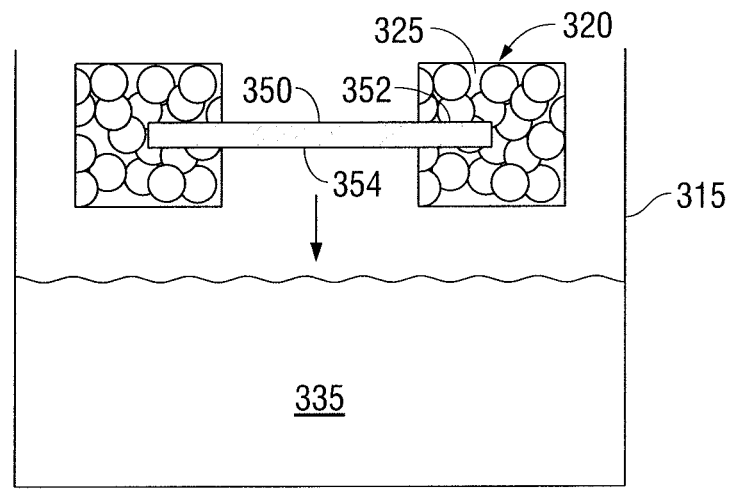
FIGS. 3A-3C schematically show the application of a first hydrogel precursor to a mesh implant as described in at least one of the embodiments in the present disclosure.
Figure 3B:
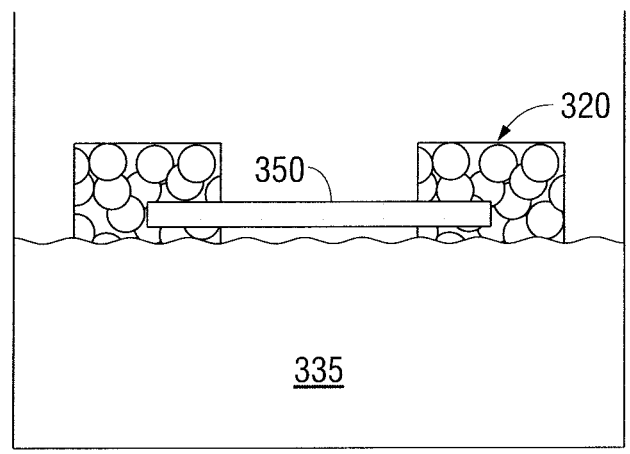
Figure 3C:
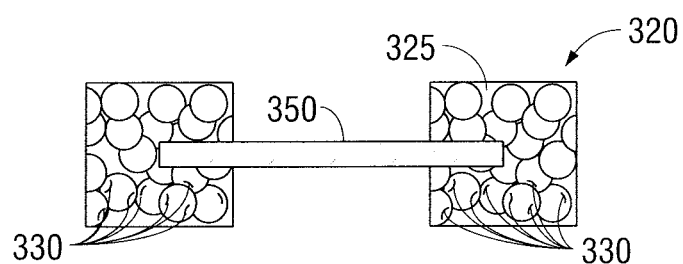

In FIG. 3A-3F, a sequence is shown wherein a first hydrogel precursor is applied within the pores of a porous substrate and a second hydrogel precursor is applied to a second portion of the porous substrate following the incorporation of the mesh into the implant. In FIG. 3A, porous substrate 320 is a foam having a plurality of pores 325 defined therein. First portion 352 of mesh 350 is embedded in porous substrate 320 and second portion 354 of mesh 350 is free of porous substrate 320. First solution 335, which includes a first hydrogel precursor dissolved in a solvent, is stored in container 315. In FIG. 3B, porous substrate 320 is dipped into first solution 335. Upon removal, the implant is dried, removing the solvent from first solution 335 and depositing particles that include the first hydrogel precursor 330 within pores 325 of substrate 320, as shown in FIG. 3C.

Figure 3D:
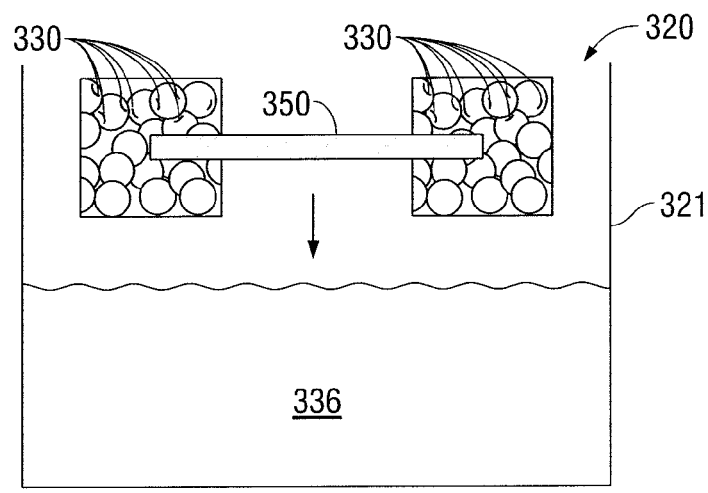
FIGS. 3D-3F schematically show the application of a second hydrogel precursor to a mesh implant as described in at least one of the embodiments in the present disclosure.
Figure 3E:
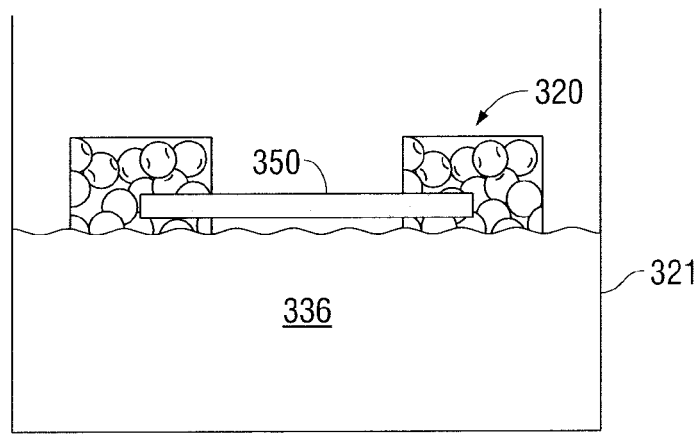
Figure 3F:
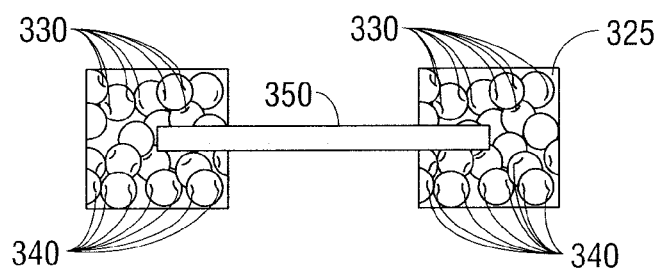

In FIGS. 3D and 3E, porous substrate 320 which contains particles of first hydrogel precursor 330 is inverted and dipped into container 321 which include second solution 336. Second solution 336 includes a second hydrogel precursor dissolved in a solvent. Upon removal, the implant is dried, removing the solvent from second solution 336 and depositing particles that include the second hydrogel precursor 340 within pores 325 of substrate 320, as shown in FIG. 3F. In the embodiments shown, the first and second hydrogel precursors are not directly applied to mesh 350. However, in embodiments, the first and/or second hydrogel precursors may also be applied to portions of the mesh.

Figure 4A:
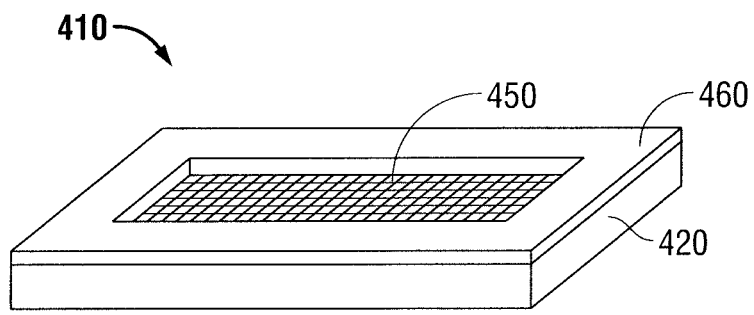
FIG. 4A shows a perspective view of an alternative embodiment of a mesh implant according to the present disclosure.
Figure 4B:
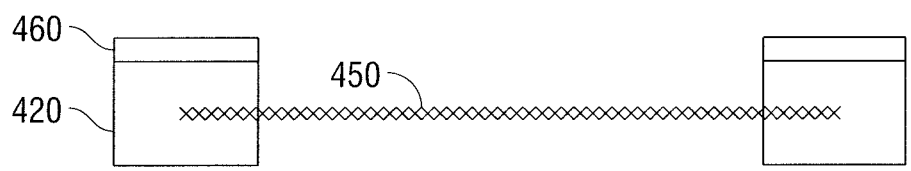
FIG. 4B shows a cross-sectional view of an alternative embodiment of a mesh implant according to the present disclosure.
Figure 4C:
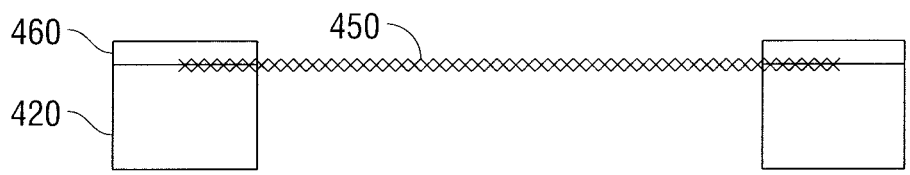
FIG. 4C shows a cross-sectional view of an alternative embodiment of a mesh implant according to the present disclosure.

Turning to FIG. 4A, implant 410 includes porous substrate 420, mesh 450 and film 460. Porous substrate 420 includes a first hydrogel precursor and film 460 includes a second hydrogel precursor. In some embodiments, mesh 450 may be incorporated into porous substrate 420 during the lyophilization process (see FIG. 4B). In other embodiments, mesh 450 may be incorporated into implant 410 after the formation of porous substrate 420 and prior to the application of film 460 thereby being positioned between substrate 420 and film 460 (see FIG. 4C). It is envisioned that a melt of the second hydrogel precursor may be positioned on top of the porous substrate after the mesh is incorporated. Upon cooling, the melt of the second hydrogel precursor solidifies to form a film over at least a portion of the substrate and/or the mesh.

Figure 5A:
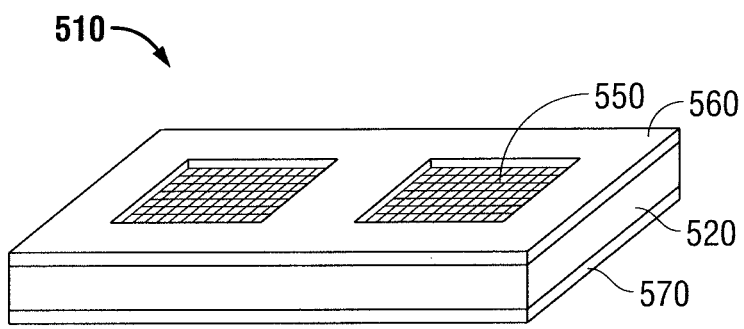
FIG. 5A shows a perspective view of one embodiment of a mesh implant according to the present disclosure.
Figure 5B:
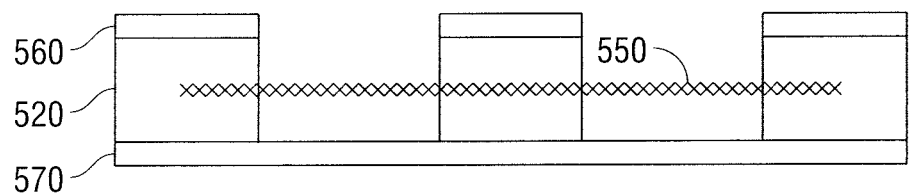
FIG. 5B shows a cross-sectional view of the implant of FIG. 5A as described in at least one of the embodiments in the present disclosure.
Figure 6:
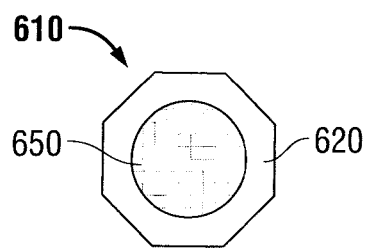
FIGS. 6-9 show top views of mesh implants as described in at least one of the embodiments in the present disclosure.

Implant 510 of FIGS. 5A and 5B, includes porous substrate 520 which extends around the perimeter of mesh 550 and also across a central portion of mesh 550. A first hydrogel precursor is also contained within porous substrate 520. Film 560 includes a second hydrogel precursor and is positioned on top of at least a part of porous substrate 520. In addition, implant 510 includes a barrier layer 570. As shown, the barrier layer is spaced apart from the mesh thereby creating a space for tissue to grow around the mesh following implantation. However, in embodiments, a portion of the mesh may also be in contact with the barrier layer.

Barrier layer 570 may be made from any suitable antiadhesive material suitable for implantation. Some examples include, but are not limited to, hydrophilic polymers such as poly(vinyl pyrrolidone), carboxymethyl cellulose, hyaluronic acid, polyethylene oxide, poly vinyl alcohols, and combinations thereof.

Figure 7:
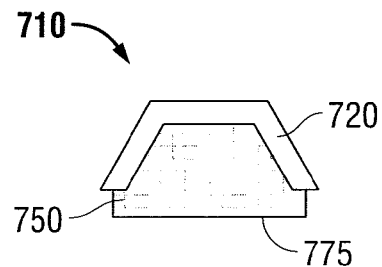

As depicted in FIGS. 6-10, various designs of the implants described herein are shown. For instance in FIG. 6, implant 610 is octagonal in shape and porous substrate 620 surrounds the perimeter of mesh 650. It is envisioned that the implant may be formed into any shape, size and/or dimension. In embodiments, the porous substrate may only extend along a portion of the perimeter of the mesh as shown in FIG. 7, wherein mesh 750 includes a free edge 775 which does not include porous substrate 720 and is free to be rolled or further tacked into position.

Figure 8:
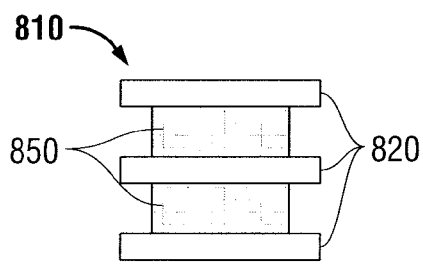
Figure 9:
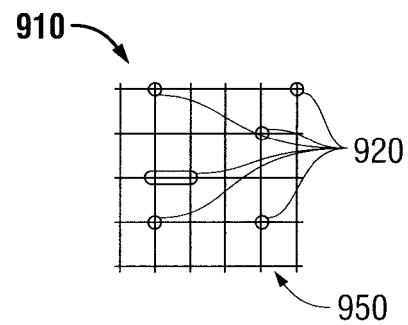

In still other embodiments, as shown in FIGS. 8 and 9, the porous substrate 820, 920, respectively, are intermittently dispersed along portions of mesh 850, 950, respectively. More specifically, implant 810 includes a plurality of strips of porous substrate 820 positioned intermittently along portions of mesh 850. In FIG. 9, implant 910 includes a plurality of islands of porous substrates 920 intermittently positioned along portions of mesh 950. Of course, each of the implants shown in FIGS. 6-9 also include a first hydrogel precursor and a second hydrogel precursor in particle, foam and/or film format, along with the other optional elements such as a barrier layer, a bioactive agent, and the like.

Figure 10:
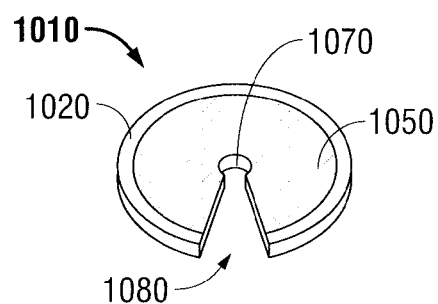
FIG. 10 shows a perspective view of yet another embodiment of a mesh implant according to the present disclosure.

In still other embodiments, the implants described herein may include at least one slit. As shown in FIG. 10, implant 1010 includes mesh 1050 having slit 1080 which extends generally from the center of mesh 1050 to an outer perimeter of implant 1010. Porous substrate 1020 extends around the perimeter of implant 1010. In addition, barrier layer 1070 is positioned along a perimeter of slit 1080 to prevent adhesions of tissue to implant 1010.

It should be understood that rather than a foam, as shown in FIGS. 1-10, the porous substrate may be a fibrous structure. Thus, in embodiments, the porous substrate may be a fibrous structure, i.e., a woven or non-woven structure. The first and second hydrogel precursors may be applied to a fibrous porous substrate using substantially the same techniques described above with respect to the foam porous substrate. Accordingly, as with the foam porous substrates described above, where the porous substrate is fibrous, the first and/or second hydrogel precursors may be applied, for example as particles deposited from a solution, non-porous films formed by drying a film-forming solution, or as a foam applied to at least a portion of the fibrous porous substrate.

It will be understood that various modifications may be made to the embodiments disclosed herein. For example, more than two precursors may be applied to the porous substrate to form the implant. As another example, the first and second precursors may each be applied to the porous substrate as a film. Thus, those skilled in the art will envision other modifications within the scope and spirit of the claims.

What is claimed is:

1. An implant comprising:
   a porous substrate;
   a first hydrogel precursor and a second hydrogel precursor applied to the porous substrate; and
   a mesh having a first portion embedded within the porous substrate and a second portion exposed for tissue contact, wherein the porous substrate is positioned around a perimeter of the mesh.

2. The implant of claim 1 wherein the porous substrate is a foam.

3. The implant of claim 1 wherein the mesh is a knitted textile.

4. The implant of claim 1 wherein the porous substrate is made from a bioabsorbable material.

5. The implant of claim 1 wherein the porous substrate is made from a material selected from the group consisting of collagen, chitosan, oxidized cellulose and combinations thereof.

6. The implant of claim 1 wherein the mesh is made from a non-bioabsorbable material.

7. The implant of claim 1 wherein the mesh is made from polypropylene.

8. The implant of claim 1 wherein the first hydrogel precursor is selected from the group consisting of particles, a foam, a film and combinations thereof.

9. The implant of claim 1 wherein the second hydrogel precursor is selected from the group consisting of particles, a foam, a film and combinations thereof.

10. The implant of claim 1 further comprising an adhesion-barrier.

11. The implant of claim 1 further comprising a bioactive agent.

12. An implant comprising:
    a porous substrate;
    a first hydrogel precursor applied to the porous substrate;
    a film containing a second hydrogel precursor, wherein the film is applied to at least a portion of the porous substrate; and
    a mesh having a first portion in contact with the porous substrate and a second portion exposed for tissue contact, wherein the porous substrate is positioned around a perimeter of the mesh.

13. The implant of claim 12 wherein the porous substrate is a foam.

14. The implant of claim 12 wherein the mesh is a woven textile.

15. The implant of claim 12 wherein the mesh is a non-woven textile.

16. The implant of claim 12 wherein the porous substrate is made from a bioabsorbable material.

17. The implant of claim 12 wherein the porous substrate is made from a material selected from the group consisting of collagen, chitosan, oxidized cellulose and combinations thereof.

18. The implant of claim 12 wherein the mesh is made from a non-bioabsorbable material.

19. The implant of claim 12 wherein the mesh is made from polypropylene.

20. The implant of claim 12 wherein the first hydrogel precursor is selected from the group consisting of particles, a foam, a film and combinations thereof.

21. The implant of claim 12 further comprising a slit defined therein.

22. The implant of claim 12 further comprising an adhesion barrier layer.

23. The implant of claim 12 further comprising a bioactive agent.

* * * * *